US007604587B2

(12) United States Patent
Manska et al.

(10) Patent No.: US 7,604,587 B2
(45) Date of Patent: Oct. 20, 2009

(54) NON-CONSTRICTIVE VIBRATION DEVICE

(76) Inventors: Wayne E. Manska, 1921 Kellogg Dr., Anaheim, CA (US) 92807; Phyllis D. Manska, 1921 Kellogg Dr., Anaheim, CA (US) 92807

( * ) Notice: Subject to any disclaimer, the term of this patent is extended or adjusted under 35 U.S.C. 154(b) by 1374 days.

(21) Appl. No.: 09/775,038

(22) Filed: Feb. 1, 2001

(65) Prior Publication Data

US 2002/0103415 A1 Aug. 1, 2002

(51) Int. Cl.
*A61F 5/00* (2006.01)
(52) U.S. Cl. .......................................................... 600/38
(58) Field of Classification Search ............. 600/38–41; 601/46, 79
See application file for complete search history.

(56) References Cited

U.S. PATENT DOCUMENTS

| | | | |
|---|---|---|---|
| 734,213 | A | 7/1903 | Barnes |
| 2,024,983 | A | 12/1935 | Street |
| 3,461,863 | A | 8/1969 | Sullinger |
| 3,504,665 | A | 4/1970 | Bakunin |
| 3,633,572 | A | 1/1972 | Wiggins |
| 3,773,040 | A | 11/1973 | Gavrilovich |
| 4,203,432 | A | 5/1980 | Koch |
| 5,836,865 | A | 11/1998 | Ritchie |
| 5,997,469 | A | 12/1999 | Northcutt |

OTHER PUBLICATIONS

Xandria Collection Summer Sale Aug. 2000; p. 6.*
"Statistics on Penis Sizes" by: Kinsey Institute of Sex Research Web Address: www.surgeon.org/surgeons/male/stats.
"Statistics on Penis Sizes" by: Kinsey Institute of Sex Research Web Address: www.surgeon.org/surgeons/male/stats, Oct. 23, 2000.

* cited by examiner

*Primary Examiner*—John P Lacyk

(57) ABSTRACT

A versatile vibrating sexual enhancement device for use by either men or women individually, or by both during sexual intercourse. The device comprises a phallic portion that contains a vibrator therein and a loop portion comprised of an elastomeric material. The loop portion is configured to encircle erect penises of various sizes without causing circumferential constriction thereto, thereby being comfortable as well as being easy to install and remove. Also, the loop portion is slidable on various sized penises, which even further increases the utility of the device during different sex acts. The device includes a controller that serves to turn the vibrator on and off. In certain embodiments the controller is remote from the device being connected thereto by a pair of electrical wires. In other embodiments the controller is located within the phallic portion of the device.

45 Claims, 11 Drawing Sheets

ON
OFF 10
10
110
112
114
120
122
140
154
158
159
160
161
164
165
166
167
168
169
170
172a
172b
174a
174b
176
178
D3
D4

ON
OFF
D7
W5
L5
310
320
322
323
324
326
328a
328b
330a
330b
334
336
337
340
352
354
380
382
384a
384b
386
388
389a
389b
4
22
23
25

NON-CONSTRICTIVE VIBRATION DEVICE

FIELD OF THE INVENTION

This invention relates to vibrating sexual enhancement devices designed to increase sexual stimulation by either men or women and additionally to those devices designed to increase mutual sexual gratification by couples during sexual intercourse.

BACKGROUND OF THE INVENTION

There historically have been many prior art devices developed to improve or aid sexual gratification, both for men and women. The devices designed for use by women are typically phallic in form and may or may not include a vibration device within. Those without a vibrator are intended for vaginal penetration and stimulation while those that vibrate are also intended for vaginal penetration and stimulation and additionally for clitoral and g-spot stimulation. Although these phallic shaped devices may be used for clitoral stimulation during intercourse, they must be hand held at such times, which limits the possible positions and comfort of one or both partners. Also, during intercourse, such devices only stimulate locally and cannot stimulate the entire region surrounding the vagina.

Prior art devices designed for use by men, especially those suffering from some degree of impotence, are commonly in the form of a round constrictive ring that tightly surrounds the base of the penis. These devices are typically not intended to directly sexually stimulate or gratify either the man or his sex partner. Instead, they are primarily intended to improve erectile dysfunction problems of the man by trapping venous blood in the penis by means of localized constriction thereby aiding in the engorgement of the penis. A problem with these devices is that when sized to be tight enough to be effective for their intended purpose they can be quite uncomfortable. Another problem is that constrictive rings can cause vascular damage and/or other physiological problems if they are too tight and/or they are left on for too long. Yet another problem with many such devices is that they are difficult to install and remove from the penis. Also, since different men's erect penises vary greatly in girth it is often difficult to obtain a correctly sized ring. This is best understood in accordance with a study conducted by Kinsey Institute of Sex Research. In this study men's erect penises varied in girth from 1.5 inches to 6.75 inches with a mean girth of about 5.0 inches. In an attempt to address the problem of providing rings that will fit different sized penises there have been developed various prior art constrictive ring devices that are adjustable. However these rings are often comprised of several parts that can be cumbersome to assemble and to correctly size. Also, except for sizing, they still have the previously mentioned inherent problems of non-adjustable rings.

Although there are some constrictive rings that have protuberances (both with and without vibrators attached) for the purpose of clitoral stimulation, the ring itself is still uncomfortably tight and awkward to install and remove which can hamper the flow and spontaneity of various sex acts. Another problem is that these rings are not slidable on the penis but instead remain stationary at the base of the penis where they are normally placed. This limits their versatility by precluding the possibility of maintaining continuous stimulating contact with the woman's vulva while the man's penis reciprocates in the woman's vagina during intercourse.

Accordingly, there is a need in the art for a versatile sexual enhancement device that is sexually stimulating to either a man or a woman individually or to both simultaneously during sexual intercourse, and additionally a device that is easy to install and remove from a man's erect penis, and also one that is slidable on a man's erect penis.

SUMMARY OF THE INVENTION

The present invention is a versatile sexual gratification device that can be used for sexual stimulation by either a man or a woman individually or to both simultaneously during the act of sexual intercourse.

In the preferred embodiment the device comprises a proximally disposed generally teardrop or football shaped loop portion and an attached distally disposed generally phallic shaped phallic portion both of which are made of an elastomeric material such as latex, silicone or vinyl. The loop portion is essentially a deformed cylinder that may be either solid or tubular. Both the loop portion and the phallic portion are bilaterally symmetrical to a first plane of symmetry and also to a second plane of symmetry wherein the first and second planes of symmetry are perpendicular to one another. The second plane of symmetry may be either straight or slightly curved.

The loop portion comprises a proximal portion, a distal portion, and two symmetrically disposed lateral portions therebetween. The proximal portion has a first radius and the lateral portions each have a larger second radius that converge at the distal portion which is attached to the phallic portion of the device. The proximal portion and lateral portions have a continuously round cross-section approximately 0.75 inch in diameter. The innermost surface of the loop portion defines an opening that is preferably at least 1.5 times as long along the intersection of the planes of symmetry as it is at its widest point and the perimeter of the opening is at least 6.0 inches long. Preferably the width of the opening is less than 1.2 inches, which assures bilateral contact of the lateral portions with penises having a girth between 3.7 inches and 6.0 inches. In other words, when the width of the loop opening is less than the diameter of the penis, the lateral portions gently grip opposite sides of the penis. This results in greater stimulation to the man when the vibrator is activated as compared to the case where the loop opening width is greater than the penis diameter. Also, more vibration is imparted to the penis itself, which even further enhances stimulation felt by the woman when the device is used during intercourse. Since the loop portion is constructed of an elastomeric material it can readily expand laterally and thus can deform to encircle various size penises up to a girth equal to the perimeter of the opening without stretching along its length. In other words, when the loop portion is placed on penises up to 6.0 inches in girth the entire length of the loop's inner surface will not be in contact with the entire circumference of the penis. Instead, a portion of the loop's inner surface will remain disengaged from the penis whereby the inner surface of the loop portion and the surface of the penis will define at least one free space. Smaller girthed penises will leave a larger free space and conversely, larger girthed penises will leave a smaller free space. In any case, as long as a free space remains, stretching along the loop portion does not occur. Accordingly, circumferential constriction to the penis does not occur which alleviates the inherent problems associated with prior art constrictive rings. Although the above referenced study on penis sizes indicates that penises vary in girth from less than 3.7 inches to more than 6.0 inches the above-described preferred embodiment of the loop portion is intended for optimal use by the vast majority of men having penises within this range. For those few men with penises larger than 6.0 inches in girth it is recommended that proportionally larger loop portions be provided. And to provide an improved fit for those men with penises smaller than 3.7 inches in girth, a means can be provided that encircles and constrains a prescribed distal length of the lateral portions thereby effecting a reduction in both the width and the perimeter of the loop opening.

The phallic portion of the device is preferably generally round in cross section along its entire length and has a spherical radius at its distal end. It may be cylindrical or it may exhibit gradually varying diameters along its length in which case it may be either somewhat tapered or corrugated. When viewed along the second plane of symmetry perpendicular to the intersection of the first and second planes of symmetry the phallic portion may be curved somewhat in which case the second plane of symmetry is similarly curved. The phallic portion is preferably at least 3.0 inches long, which assures its contact with the most sensitive areas just inside the woman's vagina when the device is used for vaginal penetration and stimulation.

The device includes an electrically powered vibrator for the purpose of increased stimulation during use. Such vibrators are commonly available and are well known in the art for their stimulation enhancement characteristics. The vibrator comprises an electric motor that has an eccentric weight attached to its shaft, which causes the vibrator to vibrate when the shaft rapidly rotates. The vibrator is located within the proximal end of the phallic portion adjacent the loop portion. This substantially centralized location assures that vibrations are optimally imparted to both the phallic portion and the loop portion. The vibrator is connected via electrical conductors to a controller whereby the controller includes a battery compartment, a battery, and an electrical switch that serves to turn the motor on and off. In certain embodiments of the invention the controller is located within the phallic portion of the device. In these cases at least a portion of the phallic portion is detachable from the loop portion thereby providing access to the battery compartment. In other embodiments the controller is located remotely from the device being connected thereto by a pair of electric wires. In this case the wires enter the device at the distal portion of the loop portion so as not to interfere with uses of the phallic portion such as vaginal penetration. Alternatively, the connection between the device and a remotely disposed controller may be wireless, i.e. radio controlled, in which case both the device and the controller contain a battery compartment.

As it is the general nature of elastomeric material surfaces to have high coefficients of friction with other surfaces it is recommended that the present invention be used in conjunction with a biocompatible lubricant. Accordingly, and especially with the aid of a lubricant, the embodiments described herein not only permit ease of installation and removal of the loop portion of the device from a man's erect penis but also readily permit axial movement of the penis within the opening of the loop portion. In fact, since the loop portion is relatively loose on the man's penis, it can remain in contact with the woman's vulva during intercourse, being held there either by gravity, or by hand by either partner, or by a harness. In these instances the man's penis can move freely back and forth within the loop while the woman experiences continuous stimulation from the vibrating device.

The above-described device may also be used for sexual gratification in other ways. For example, it may be hand held by the loop portion while using the phallic portion to stimulate various external erogenous areas such as a woman's breasts or vulva or a man's genitals. Or, the phallic portion may be used for vaginal penetration and stimulation and g-spot stimulation. Conversely, the device may be held by the phallic portion while the loop portion is used to stimulate erogenous areas of either a man or a woman. Also, the loop may be placed around a man's penis for stimulation during such acts as masturbation or felatio. At such times, the phallic portion of the device may be positioned for simultaneous testicular stimulation. Or, during intercourse, while the loop portion stimulates a woman's vulva, the phallic portion may be positioned to simultaneously stimulate her anus. The device may additionally include means such as openings for the attachment of a harness whereby the harness is used to hold the device in place in front of a woman's vagina during intercourse. The harness comprises straps that encircle the woman's waist, hips and/or legs to appropriately position the device in place.

In an alternate embodiment of the invention the phallic portion may be reduced in size to the extent that it minimally encloses the vibrator. In this case the device is intended only for those instances where in encircles the man's penis during uses such as intercourse.

The device can be manufactured, for example, by molding an appropriate elastomeric material whereby the phallic portion and the loop portion are integral to one another and are inseparable. In this case the vibrator is encapsulated within the phallic portion and the controller is located remotely from the device. On the other hand, both the vibrator and the controller can be located within the device, in which case all or part of the phallic portion is detachable for the purpose of providing access to the battery compartment. In this case, the loop portion can be manufactured by multiple methods. For example, it can be molded in its final configuration using a suitable elastomeric material. Alternatively, it can be formed by bending an appropriate length of cylindrical elastomeric material, either solid or tubular, such that the two ends converge whereat they are physically attached by mechanical means and/or by adhesives to the proximal end of the phallic portion. If the cylindrical material is either solid, or tubular with thick walls, the resulting loop portion is substantially teardrop shaped. However, if the cylindrical material is tubular with thin walls, a kink occurs where stresses are the highest at the middle of the tube's length which results in a substantially football shaped loop portion. For a given material, tubular loop portions are lighter and a bit more compliant than solid loop portions. This is because the walls collapse somewhat during various uses. This results in more comfort to the man when the loop portion is placed around his penis and also provides a more yielding, stimulating cushion when the man deeply penetrates the woman during intercourse. However, satisfactory solid loop portions can be made from acceptably compliant materials. Therefore, for purposes of this invention, loop portions may be either solid or tubular and either teardrop or football shaped.

Accordingly, it is an object of the present invention to provide a vibrating sexual enhancement device that can be conveniently and comfortably used during sexual intercourse that is simultaneously sexually stimulating to both partners and additionally helps the woman more readily achieve orgasm.

Another object of the invention is to provide a comfortable and sexually stimulating device that is easily installed and removed from a man's erect penis.

Yet another object of the invention is to provide a comfortable and sexually stimulating device that is slidable on a man's erect penis.

A further object is to provide a device that is simultaneously stimulating to the entire erogenous region surrounding a woman's vaginal opening. Even another object is to provide a versatile device that can at one time be used to sexually stimulate a man and at another time be used to sexually stimulate a woman.

And another object is to provide a device that imparts vibrations to erect penises of various sizes without effecting constriction.

And even another object is to provide a stimulating device that encircles a man's penis during sexual activities without the risk of injury to the man.

DESCRIPTION OF THE DRAWINGS

These and other features of the present invention may be more fully understood through reference to the drawings in which.

DESCRIPTION OF THE PREFERRED EMBODIMENTS

Figures 1, 2, 3, 4, 5, 6:
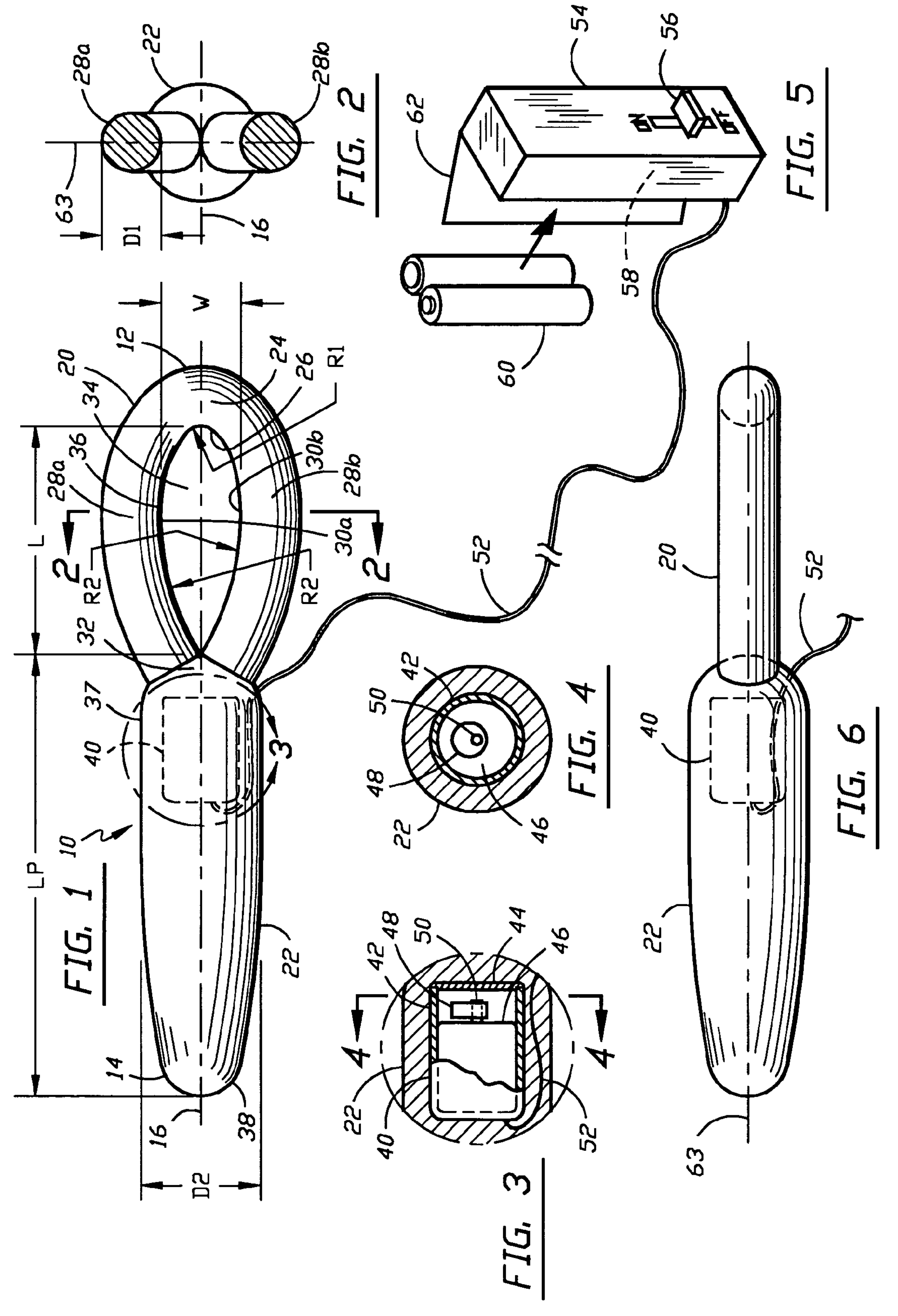
FIG. 1 is a plan view of a preferred embodiment of the invention showing a proximally disposed loop portion and a distally disposed phallic portion containing a vibrator therein, and a remotely connected controller.
FIG. 2 is a section view taken along the lines 2-2 of the loop portion of FIG. 1.
FIG. 3 is a partial section of the phallic portion of the device of FIG. 1 showing components of the vibrator.
FIG. 4 is a sectional end view of the vibrator taken along lines 4-4 of FIG. 3 showing the eccentric weight attached to the shaft of the motor.
FIG. 5 is an isometric view of a controller that serves to power the vibrator.
FIG. 6 is a side view of the device shown in FIG. 1 showing a second plane of symmetry.

Referring to FIG. 1, a plan view of a preferred embodiment of the present invention is shown comprising a sexual enhancement device 10 substantially comprised of an elastomeric material such as latex, silicone or vinyl. The device 10 has a proximal end 12 and a distal end 14 and is bilaterally symmetrical to a first plane of symmetry 16. The device 10 includes a proximally positioned loop portion 20 that is connected to, and integral with, a distally positioned phallic portion 22. The loop portion 20 is generally teardrop shaped in that it has a proximal portion 24 that has an inner surface 26 having a first radius R1, and two symmetrically disposed lateral portions 28*a*, 28*b* which have inner surfaces 30*a*, 30*b*, respectively, each of which has a second larger radius R2, that converge at a distal portion 32. The inner surfaces 26, 30*a*, 30*b* of the loop portion 20 define an opening 34 having a length L, a width W, and a perimeter 36. The length L is at least 1.5 times the width W, and the perimeter is at least 6.0 inches long. Preferably the width W of the opening 34 is 1.2 inches or less, which assures bilateral contact of the inner surfaces 30*a*, 30*b* with penises having a girth between 3.7 inches and 6.0 inches, which is representative of about 94% of men according to the above-mentioned study. The proximal and lateral portions, 24, 28*a*, 28*b*, respectively, have a continuous cross-sectional diameter D1 as represented in FIG. 2. For reasons of comfort and to assure optimal sensation to both the man and the woman without substantially reducing the potential penetration of the penis during intercourse, the diameter D1 is preferably between 0.5 and 1.0 inches.

The phallic portion 22 is generally round in cross section along its length and has a diameter D2 of approximately 1.5 inches at its proximal end 37 and therefrom it tapers somewhat toward its distal end 38 whereat it has a spherical radius. The phallic portion 22 has a length LP that is preferably between three and six inches and includes an electrically powered vibrator 40 that is embedded within the proximal end 37 adjacent the loop portion 20. FIG. 3 is a slightly enlarged partially sectioned view of the proximal end 37 of the phallic portion 22 showing the components of the vibrator 40. The vibrator 40 comprises a container 42 and a container cover 44 that serve to encapsulate a low voltage electric motor 46. The motor 46 has an eccentric weight 48 attached to its shaft 50 that causes the vibrator 40 to vibrate when the motor 46 is activated. FIG. 4 shows the eccentric disposition of the weight 48 with respect to the shaft 50. The vibrator 40 is connected via a pair of electric wires 52 to a controller 54, which is shown in isometric view in FIG. 5. The controller 54 includes a switch actuator 56 that functions to turn the vibrator 40 on and off. The controller 54 also has a battery compartment 58, which is used to store batteries 60 that serve to power the motor 46. A cover 62 that is either hinged or removable is provided for accessing the battery compartment 58.

FIG. 6 shows the device 10 is also bilaterally symmetrical to a second plane of symmetry 63, which is perpendicular to the first plane of symmetry 16 as illustrated in FIG. 2.

Figure 8:
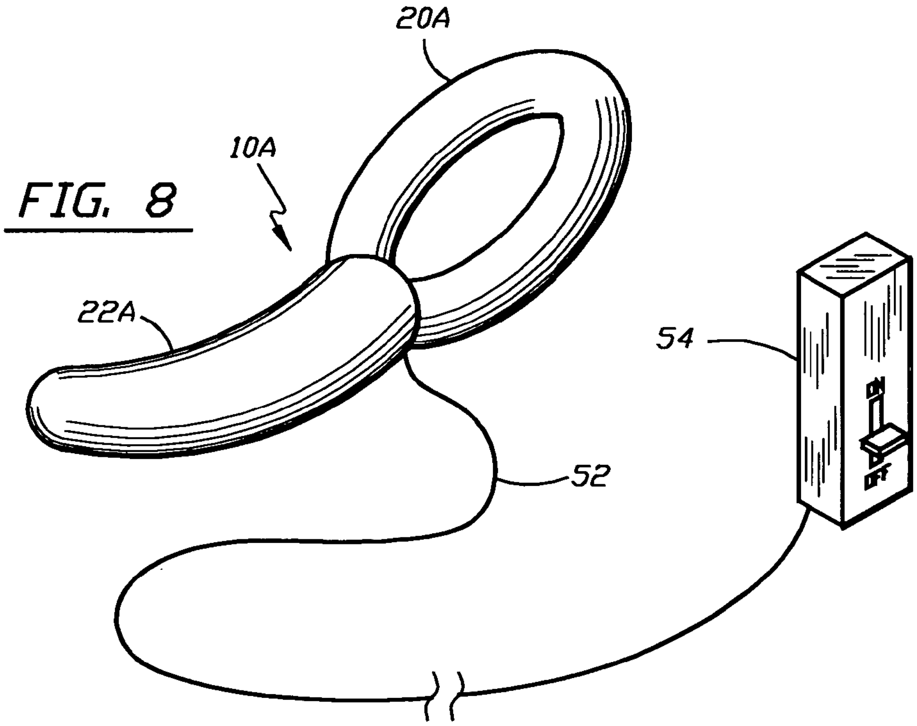
FIG. 8 is a perspective view of the device of FIG. 7.
Figure 7:
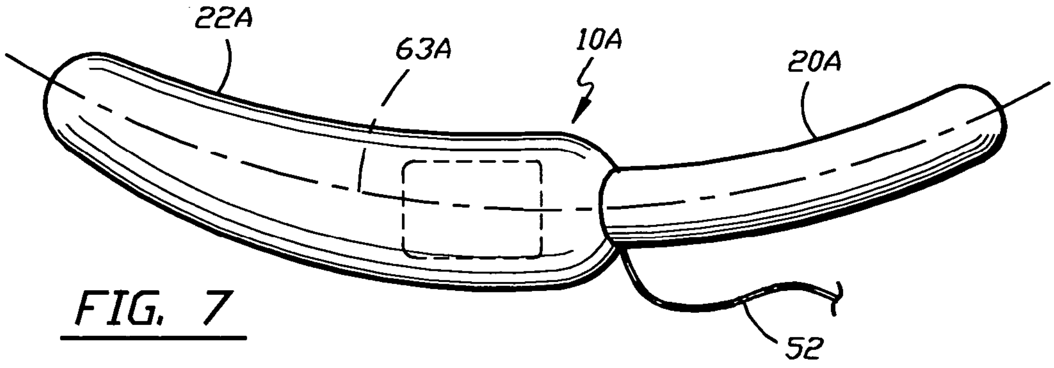
FIG. 7 is an alternative side view of the device shown in FIG. 1 whereby the second plane of symmetry is curved.

An alternative side view of the device 10 of FIG. 1 is shown in FIG. 7 whereby at least a portion of the second plane of symmetry 63A of a device 10A is curved in which case the loop portion 20A and the phallic portion 22A are similarly curved. This embodiment is illustrated in isometric view in FIG. 8, which shows the device 10A, interconnecting with the controller 54 via the electric wires 52.

Figures 9, 10, 11, 12:
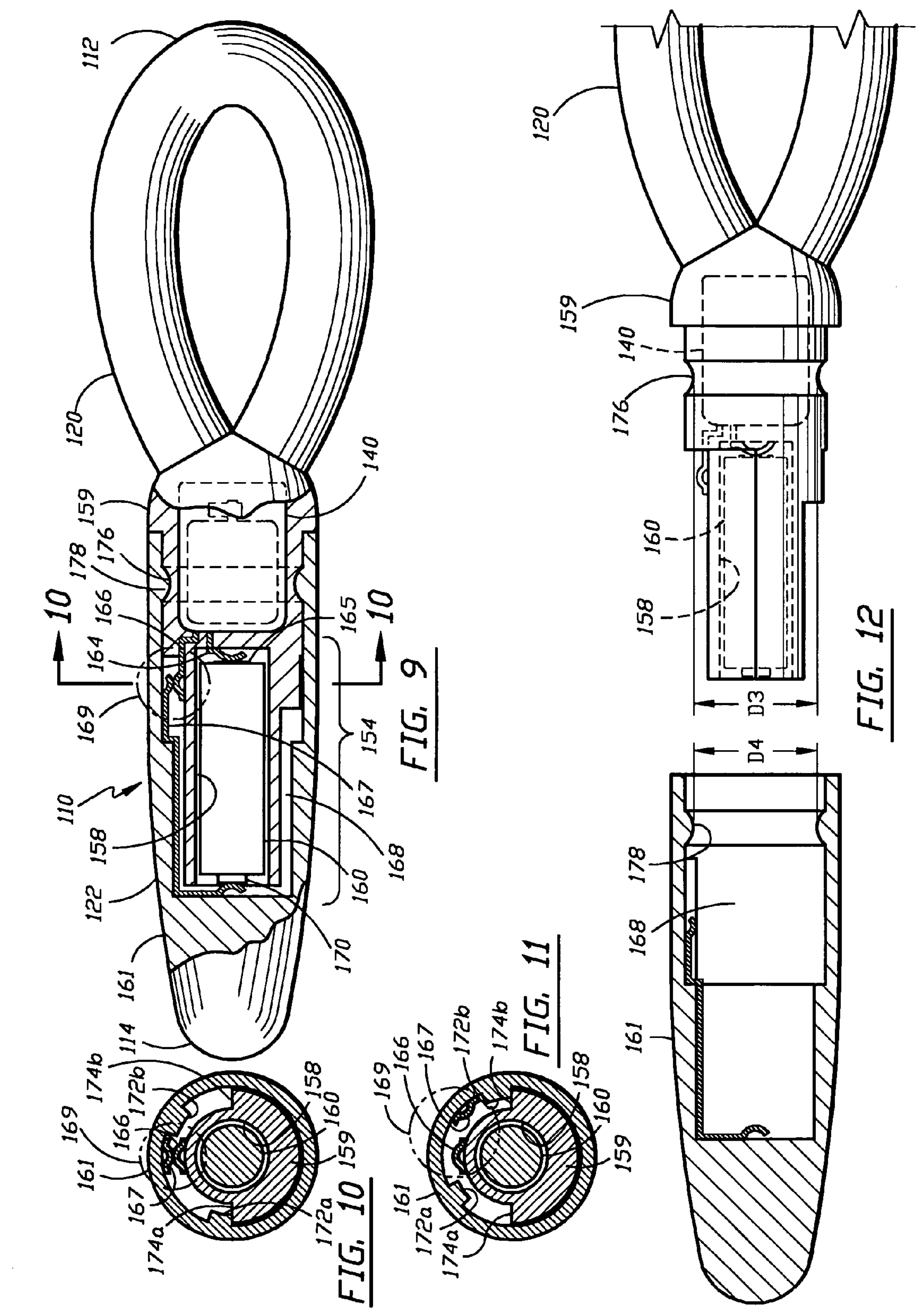
FIG. 9 is a partially sectioned plan view of an alternative preferred embodiment of the invention where both the vibrator and the controller are located within the phallic portion of the device and a portion of the phallic portion is detachable.
FIG. 10 is a section view taken along the lines 10-10 of FIG. 9 showing switching elements of the controller in an "on" position.
FIG. 11 is an alternate section view taken along the lines 10-10 of FIG. 9 showing switching elements of the controller orientated in an "off" position.
FIG. 12 shows the device of FIG. 9 whereby the detachable portion (sectional view) is detached from an inseparable portion (partial exterior view) providing access to a battery compartment.

FIG. 9 shows a plan view of another embodiment of the present invention whereby a device 110 has proximal end 112 and a distal end 114. The device 110 comprises a proximally positioned loop portion 120 and a distally positioned phallic portion 122 that comprises an inseparable portion 159 and a detachable portion 161. The inseparable portion 159 is attached to the loop portion 120, which is similar in structure to the loop portion 20 of the device 10 of FIG. 1. The inseparable portion 159 contains a vibrator 140 and a battery compartment 158 that functions to house a battery 160. A first electrical conductor 164 between the vibrator 140 and the proximal end of the battery compartment 158 is provided for the purpose of making an electrical connection between a first terminal 165 of the battery 160 and the vibrator 140. A second electrical conductor 166 is provided between the vibrator 140 and an exposed surface of the inseparable portion 159 for the purpose of intermittent contact with a third electrical conductor 167 which is positioned in a cavity 168 in the detachable portion 161 and which makes contact with a second terminal 170 of the battery 160. Accordingly, the distal end of the second electrical conductor 166 and the proximal end of the third electrical conductor 167 function as an electrical switch 169 between the vibrator 140 and the battery 160 that serves to turn the vibrator 140 on and off. FIGS. 10 and 11 show internal ribs 172*a*, 172*b* on the detachable portion 161, and abutting surfaces 174*a*, 174*b* on the inseparable portion 159 that cooperate to limit the rotation of the detachable portion 161 with respect to the inseparable portion 159 such that the vibrator 140 can readily be turned on and off. For example, FIG. 10 shows the detachable portion 161 rotated to its counterclockwise limit whereby the rib 172*a* abuts the surface 174*a* and the second electrical conductor 166 contacts the third electrical conductor 167 thereby placing the switch 169 in the "on" position. Alternatively, FIG. 11 shows the detachable portion 161 rotated to its clockwise limit whereby the rib 172*b* abuts the surface 174*b* and the second electrical conductor 166 is separated from the third electrical conductor 167 thereby placing the switch 169 in the "off" position. Accordingly, in this embodiment, the electrical conductors 164, 166, and 167, the battery compartment 158, the battery 160 and the switch 169 collectively comprise a controller 154 for the device 110.

The inseparable portion 159 includes an annular groove 176 that serves to engage an annular rib 178 on the wall of the cavity 168 of the detachable portion 161 thus providing a retaining means between the two portions 159, 161 when they are pressed together. To access the battery compartment 158, the detachable portion 161 can be detached from the inseparable portion 159 simply by pulling the two portions 159, 161 apart axially. Conversely, pressing the portions 159, 161 together axially until the annular rib 178 seats in the annular grove 176 can reassemble the device. This configuration also permits axial rotation of the detachable portion 161 with respect to the inseparable portion 159, which is important with respect to the built-in switch 169 described above. As shown in FIG. 12, the annular grove 176 of the inseparable portion 159 has a diameter D3 and the annular rib on the detachable portion 161 has a diameter D4. For purposes of optimal retention, the diameter D3 is equal to or slightly greater than the diameter D4. Although the battery compartment 158 is shown located in the inseparable portion 159 in this embodiment it is recognized that it could alternatively be located in a detachable portion (not shown). It is also recognized that the vibrator 140, which is shown positioned in the inseparable portion 159, could just as easily be positioned in a detachable portion in which case a controller may be located either within the device or remote from the device.

Figure 13:
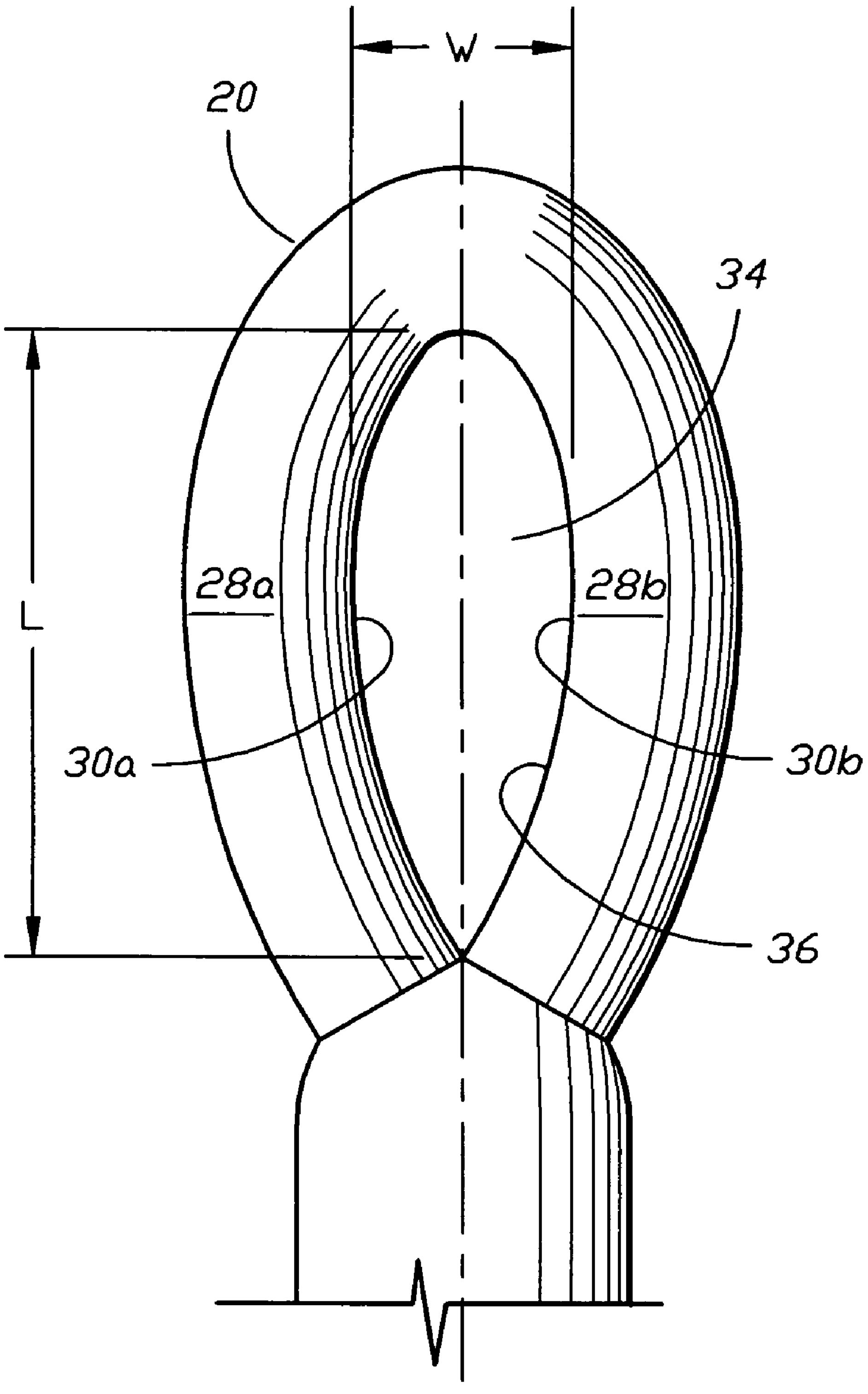
FIG. 13 is a 1/1 scale plan view of the loop portion of the device of FIG. 1 showing a nominal opening having a length, a width, and a perimeter defined by an inner surface.
Figure 16:
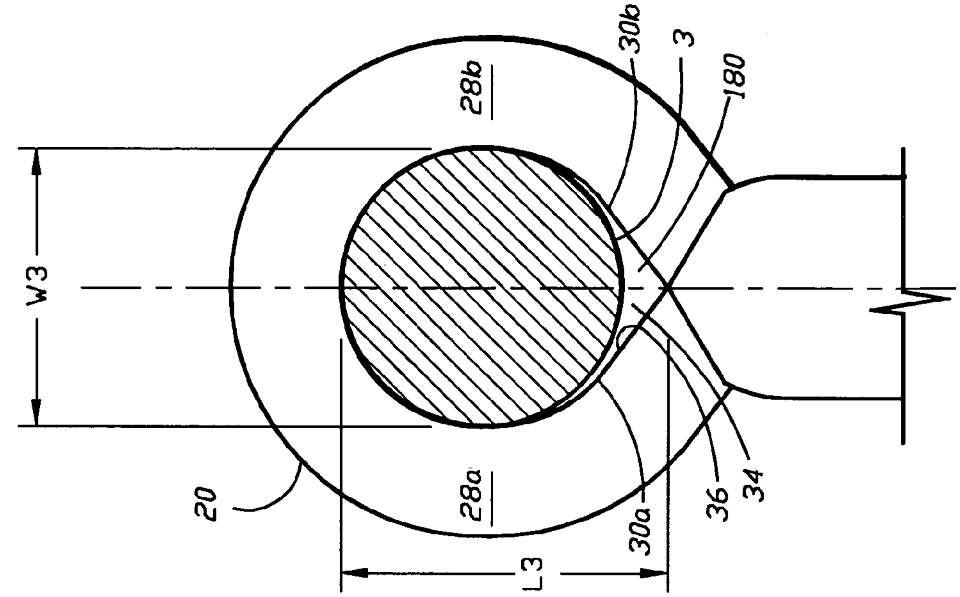
FIG. 16 is a plan view of the loop portion of the device of FIG. 1 showing a penis with a girth of 6.0 inches positioned within the opening thereby causing even further deformation of the loop portion.
Figure 15:
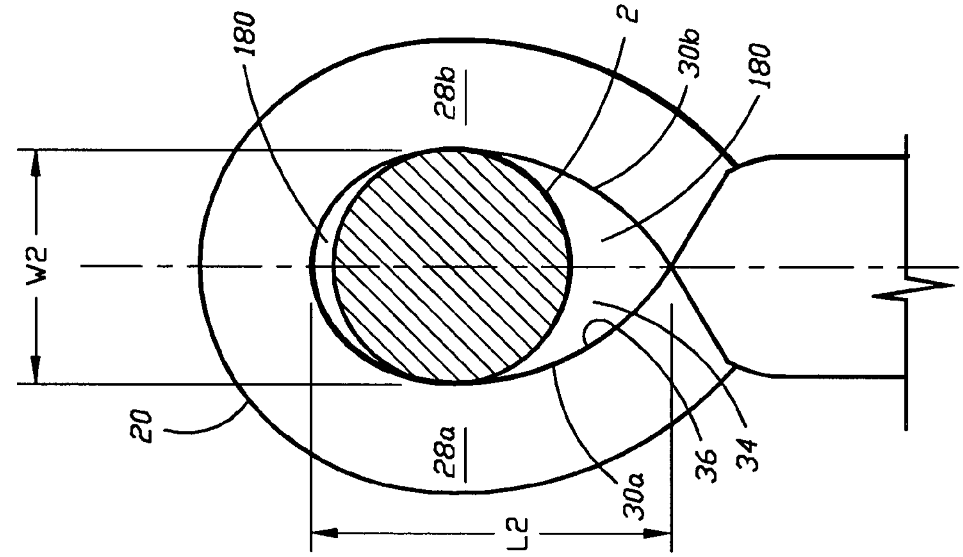
FIG. 15 is a plan view of the loop portion of the device of FIG. 1 showing a penis with a girth of 5.0 inches positioned within the opening thereby causing further deformation of the loop portion.
Figure 14:
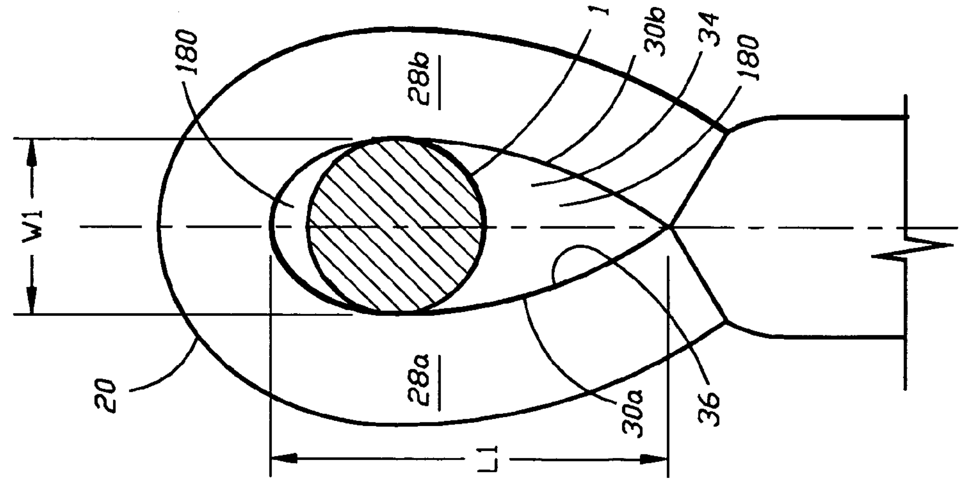
FIG. 14 is a plan view of the loop portion of the device of FIG. 1 showing a penis with a girth of 3.7 inches positioned within the opening thereby causing a deformation to the loop portion.

FIG. 13 shows at 1/1 scale the loop portion 20 of the device 10 of FIG. 1 in its nominal form whereby the opening 34 has a length L of 2.87 inches, a width W of 1.0 inch and a perimeter 36 that is 6.3 inches. FIGS. 14, 15 and 16 illustrate at 4/5 scale the deformation of the loop portion 20 of FIG. 13 when penises 1, 2, 3, respectively, having girths of 3.8 inches, 5.0 inches and 6.0 inches, respectively, are placed into the opening 34. These sizes represent the smaller 10%, the mean, and the larger 10% of penises of men referenced in the previously discussed study. In each case, the lateral portions 28*a*, 28*b* expand laterally to the extent that their inner surfaces 30*a*, 30*b* nominally bilaterally contact each penis 1, 2, or 3. At least one free space 180 remains between the perimeter 36 of the opening 34 and the surface of each penis 1, 2, or 3, which will be the case as long as the girth of the penis does not exceed the length of the perimeter 36. As long as a free space 180 remains, circumferential constriction to the penises 1, 2, 3 does not occur. It is noted that when the progressively larger penises 1, 2, 3, respectively, are in the opening 34, the width W1, W2, W3, respectively, increases to where it equals the diameter of the penis 1, 2, 3, respectively; the length L1, L2, L3, respectively, decreases; and the cross-sectional area of the opening 34 increases. However, in all cases the perimeter 36 remains substantially the same. Accordingly, this embodiment permits ease of installing and removing the loop portion 20 from the various sized penises 1, 2, 3 and also, with the aid of a lubricant, permits slidable axial movement of the penises 1, 2, 3 within the opening 34.

Figures 17, 18, 19, 20:
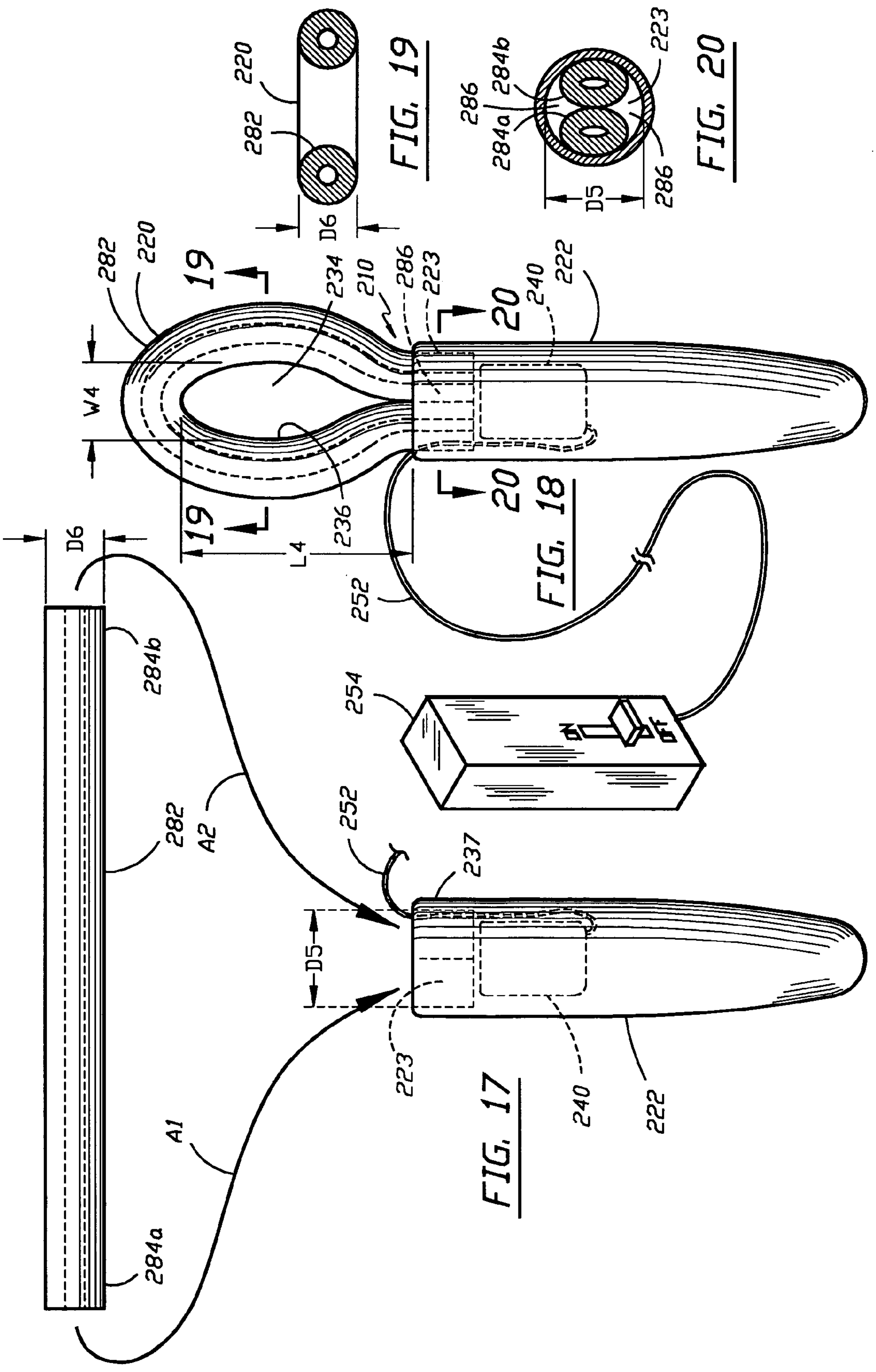
FIG. 17 shows a pre-assembled plan view of components of another alternative embodiment of the invention comprising a length of thick-walled elastomeric tubular material and a pre-formed phallic portion.
FIG. 18 shows the embodiment of the invention comprising the assembled components of FIG. 17 and a controller.
FIG. 19 is a cross sectional view of the loop portion taken along lines 19-19 of FIG. 18.
FIG. 20 is a cross sectional view taken along lines 20-20 of FIG. 18 showing ends of the loop portion seated and constrained in a recess in the proximal end of the phallic portion.

FIG. 17 shows a phallic portion 222 that has a recess 223 with a diameter D5 in its proximal end 237, and a prescribed length of an elastomeric cylinder 282 having a diameter D6 between 0.5 and 1.0 inch. The phallic portion 222 contains a vibrator 240 therein that has a pair of electric wires 252 attached for the purpose of subsequent connection to a controller (not shown). The cylinder 282 is bent and its ends 284*a*, 284*b*, are placed into the recess 223 as indicated by arrows A1, A2, which results in a loop portion 220 of another alternative device 210 shown in FIG. 18. The loop portion 220 is substantially teardrop shaped and has an opening 234 that has a length L4, a width W4 that is less than 1.2 inches, and a perimeter 236 that is at least 6.0 inches long. The cylinder 282 is tubular with thick walls as shown in FIG. 19, however it could also be solid. The diameter D5 of the recess 223 is slightly less than twice the diameter D6 of the cylinder 282, which results in the ends 284*a*, 284*b* collapsing somewhat in the recess 223 as illustrated in FIG. 20. A suitable adhesive 286 is applied between the ends 284*a*, 284*b* and the recess 223, which permanently affixes the formed loop portion 220 to the phallic portion 222. A remotely located controller 254 is provided that is connected to the vibrator 240 in the device 210 via the pair of electric wires 252.

Figures 21, 22, 23, 24, 25:
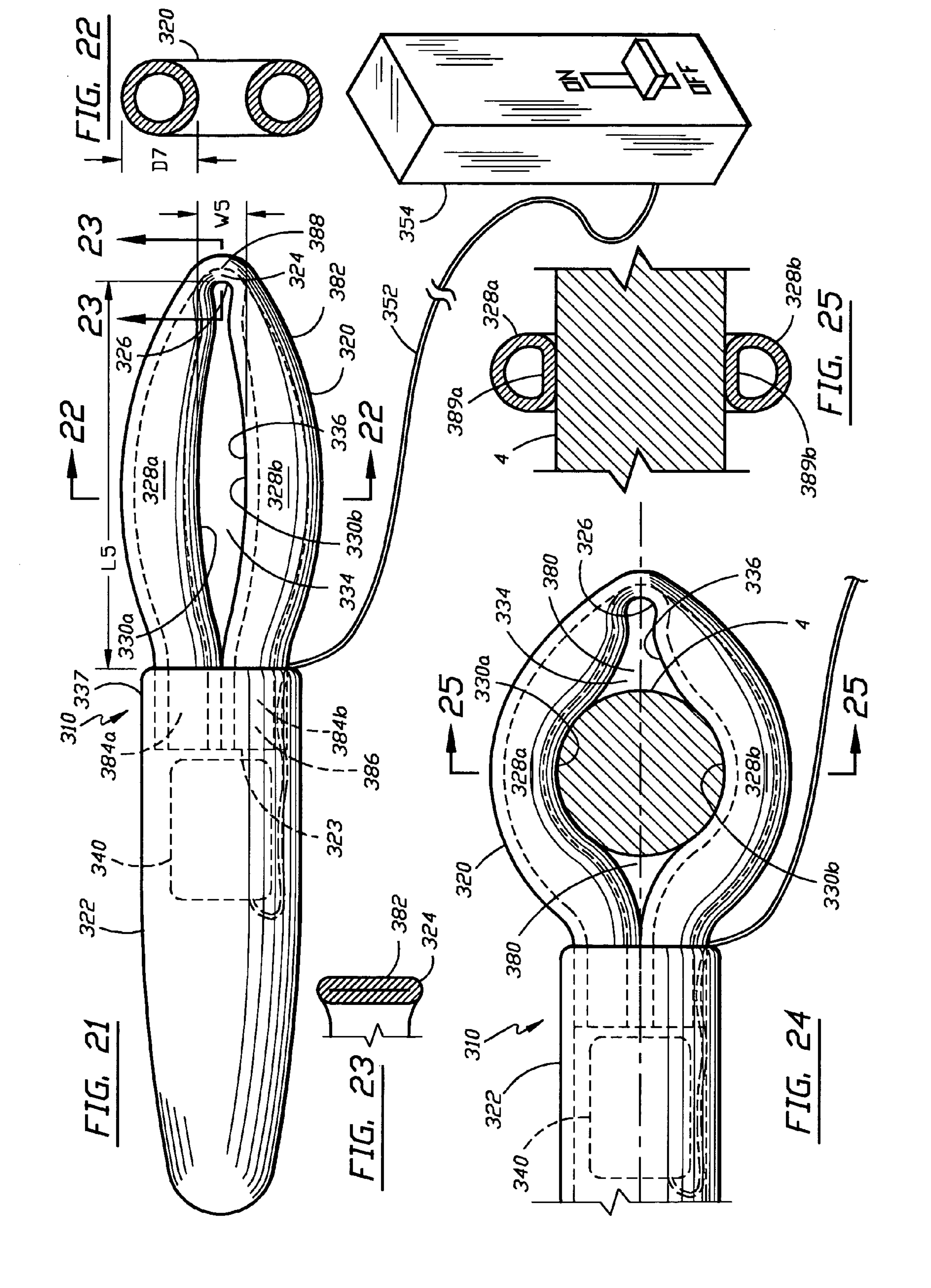
FIG. 21 is a plan view of yet another alternative embodiment of the device wherein the loop portion is comprised of a thin-walled elastomeric tube.
FIG. 22 is a sectional view of the loop portion of the device taken along lines 22-22 of FIG. 21.
FIG. 23 is a sectional view of the distal portion of the loop portion taken along lines 23-23 of FIG. 21 showing collapsing of the walls of the thin-walled tube.
FIG. 24 shows a partial view of the device of FIG. 21 whereby a penis shown in cross-section is disposed within the opening of the loop portion.
FIG. 25 is a sectional view taken along lines 25-25 of FIG. 24 showing a localized deformation of the inner walls of the loop portion adjacent the penis.

FIG. 21 shows a device 310 of yet another embodiment similar to the device 210 of FIG. 18. The device 310 includes a proximally positioned loop portion 320 and a distally positioned phallic portion 322. The phallic portion 322 preferably is between 3.0 and 6.0 inches long and has a vibrator 340 therein that has a pair of electric wires 352 connected thereto that interconnect with a controller 354. The loop portion 320 is formed from a prescribed length of cylindrical, thin-walled elastomeric tubular material 382 that has ends 384*a*, 384*b*, whereby the tubular material 382 is bent and its ends 384*a*, 384*b* are placed in a recess 323 in a proximal end 337 of the phallic portion 322 whereat they are bonded thereto with a suitable adhesive 386. The tubular material 382, which has a diameter D7 between 0.5 and 1.0 inch, is relatively thin-walled as shown in FIG. 22, as compared to the tubular material 282 of the device 210 (FIG. 18). Consequently, said forming causes the tubular material 382 to collapse at a proximal portion 324 of the loop portion 320, which results in a kink 388, which is more fully understood with reference to FIG. 23. The resulting substantially football-shaped loop portion 320 has an opening 334 defined by an inner surface 326 of the proximal portion 324 and inner surfaces 330*a*, 330*b* of lateral portions 328*a*, 328*b*, respectively. The opening 334 has a length L5, a width W5 less than 1.2 inches, and a perimeter 336. The pre-formed length of tubular material 382 is such that the resulting perimeter 336 is at least 6.0 inches long.

FIG. 24 shows at 4/5 scale a penis 4 with a girth of 5 inches positioned within the opening 334 of the loop portion 320 of the device 310. The lateral portions 328*a*, 328*b* are expanded to the extent that their inner surfaces 330*a*, 330*b* nominally bilaterally contact the penis 4. Free spaces 380, remain between the inner surfaces 326, 330*a*, 330*b*, of the opening 334 and the surface of the penis 4. The perimeter 336 remains substantially unchanged and circumferential constriction to the penis 4 does not occur. In fact, due to the compliant nature of the elastomeric material of the loop portion 320, additional compliance is provided as inner walls 389*a*, 389*b*, of the lateral portions 328*a*, 328*b* adjacent the penis 4 collapse somewhat as illustrated in FIG. 25.

Figure 29:
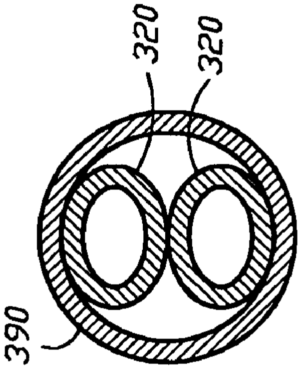
FIG. 29 is a sectional view taken along lines 29-29 of FIG. 28 showing the constraining ring constraining the distal portion of the loop portion.
Figure 27:
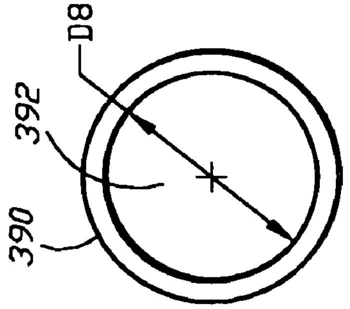
FIG. 27 is an end view of the constraining ring shown in FIG. 26.
Figure 26:
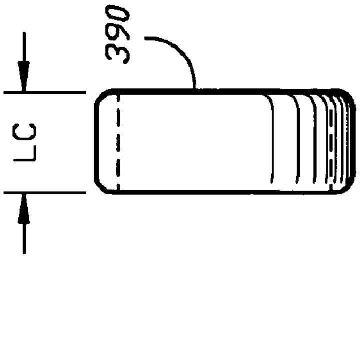
FIG. 26 is a plan view of a constraining ring that functions to reduce the size of the opening of the loop portion.
Figure 28:
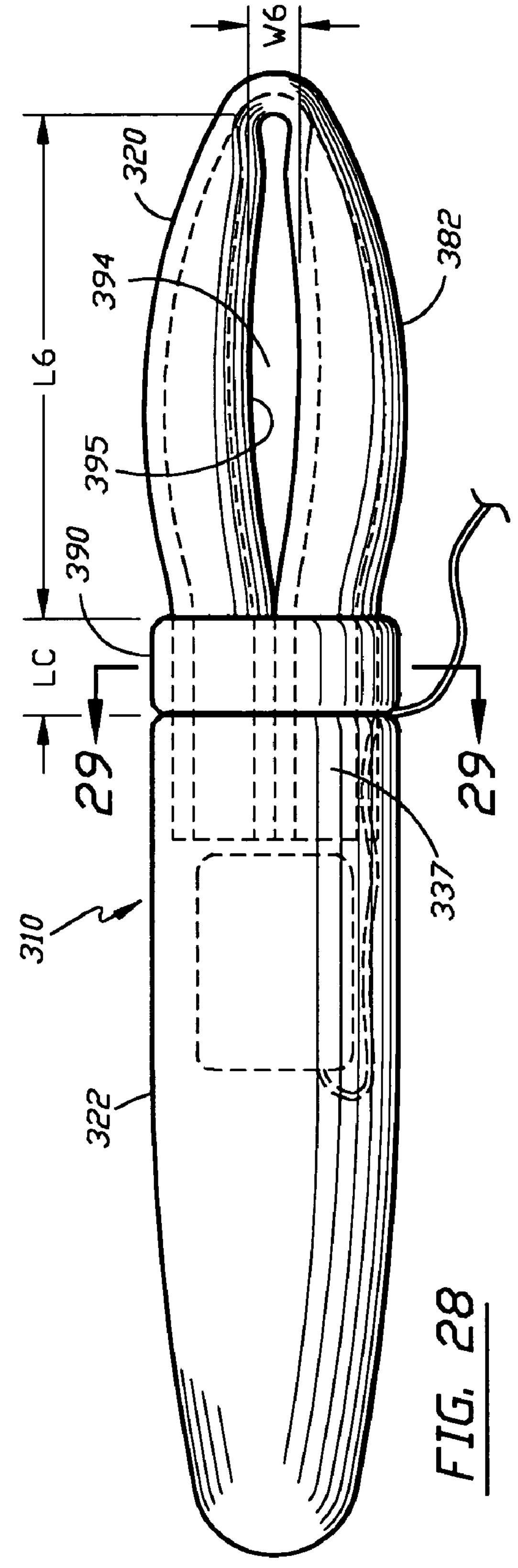
FIG. 28 is a plan view of the device shown in FIG. 21 showing the constraining ring of FIGS. 26 & 27 placed on the distal portion of the loop portion.

Although the loop portions described herein would fit virtually any penis with a girth up to 6.0 inches without causing circumferential constriction, a user may prefer a more custom fit. For this purpose a constraining ring 390 can be provided as illustrated in FIGS. 26 and 27. The constraining ring 390 has a length LC, and an aperture 392 that has an inside diameter D8 that is equal to or less than two times the diameter D7 of the tubular material 382 comprising the loop portion 320. The constraining ring 390 can be readily installed on the device 310 by simply pulling the loop portion 320 through the aperture 392 until the constraining ring 390 seats against the proximal end 337 of the phallic portion 322 as shown in FIGS. 28 and 29. When the constraining ring 390 is so placed, it locally constrains a distal length of the loop portion 320 equal to the length LC of the constraining ring 390 as shown in FIGS. 28 and 29, which in effect shortens the length L5 of the opening 334 (FIG. 21) by the same amount. This results in a smaller opening 394 having a reduced length L6. It also causes the width W5 (FIG. 21) to narrow to a new width W6 and the perimeter 336 (FIG. 21) to reduce to a new perimeter 395. Accordingly, by installing a constraining ring having an prescribed length, the size of a loop opening can be adjusted to more correctly fit smaller girthed penises. Although the constraining ring 390 is described in conjunction with the device 310, it would have equal utility with other embodiments of the present invention described herein.

Figures 30, 31, 32:
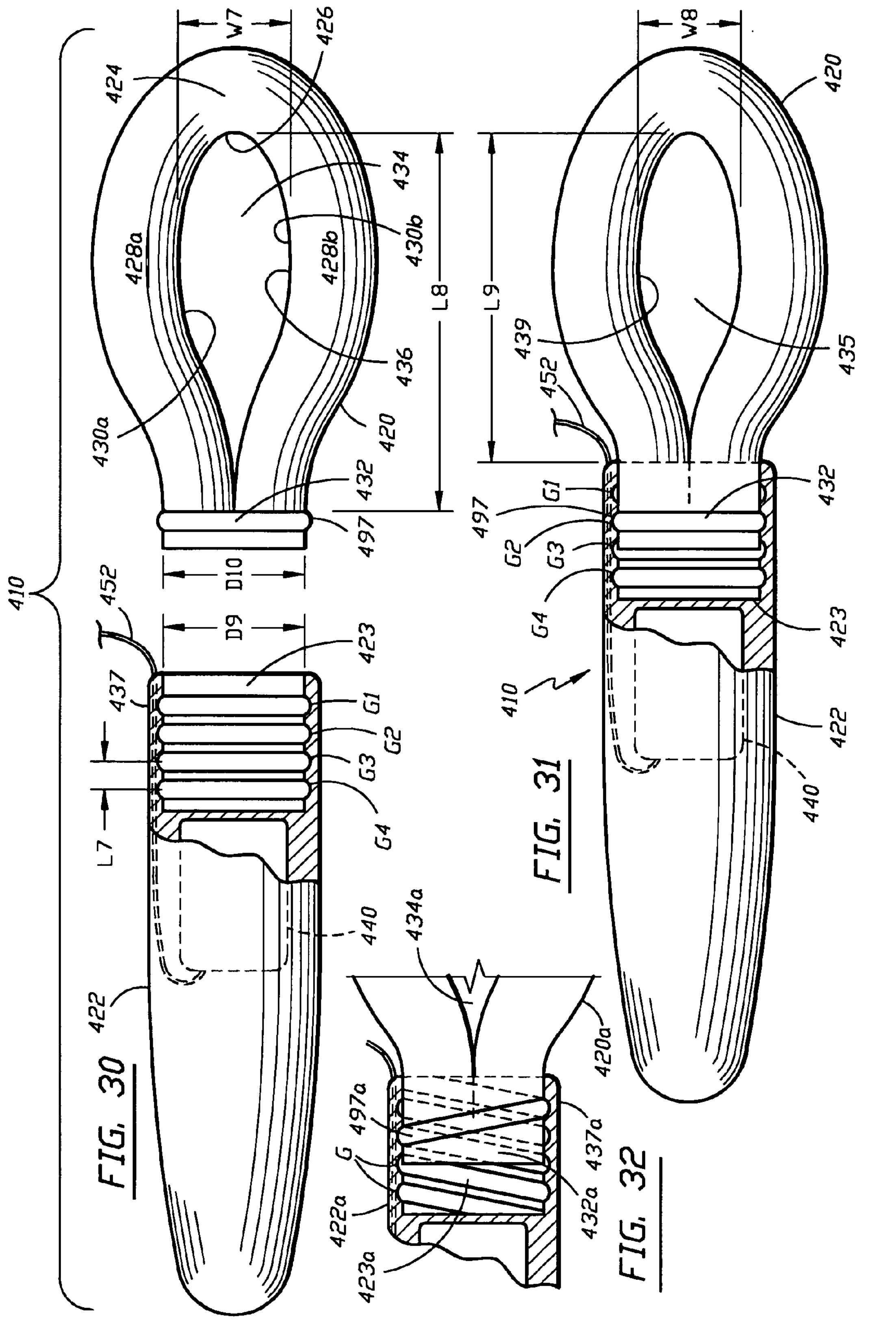
FIG. 30 shows a plan view of even another embodiment comprising a phallic portion shown partially sectioned and an attachable loop portion and a means for attachment and adjustment.
FIG. 31 shows a plan view of the loop portion and the phallic portion of FIG. 30 attached to one another and a means for varying the size of the opening in the loop portion.
FIG. 32 is a view of an alternative means for varying the size of the opening in the loop portion.

FIG. 30 shows a device 410 comprising a phallic portion 422 having a vibrator 440 positioned therein that has a pair of electric wires 452 that interconnect with a remotely disposed controller (not shown). For purposes of this invention, the controller could alternatively be positioned within the phallic portion in a manner similar to that shown in FIGS. 9-12. The phallic portion 422 has a recess 423 with an opening dimension D9 in its proximal end 437 whereby the recess 423 includes retaining/adjusting means comprising a plurality of grooves G1, G2, G3, G4, incrementally spaced at a dimension L7. The device 410 includes an attachable loop portion 420 made of cylindrical elastomeric material, which may be tubular, comprising a proximal portion 424 and two lateral portions 428*a*, 428*b* that converge at a distal portion 432. Said proximal and lateral portions 424, 428*a*, 428*b*, respectively, have inner surfaces 426, 430*a*, 430*b*, respectively, that define an opening 434 having a length L8, a width W7, and a perimeter 436 at least 6.00 inches long. The distal portion 432 has an outside dimension D10 that is equal to or greater than the opening dimension D9 of the recess 423. The distal portion 432 additionally includes a complimentary retaining/adjusting means comprising a rib 497 that is configured to snugly fit in any of the grooves G1, G2, G3, or G4. This configuration enables the user to incrementally adjust the effective length L8 and width W7 of the opening 434, and consequently the perimeter 436, by pressing the distal portion 432 of the attachable loop portion 420 into the recess 423 until the rib 497 seats in a selected groove G1, G2, G3 or G4, whereby a distal length of the lateral portions 428*a*, 428*b* is constrained by the recess 423. For example, as shown in FIG. 31, the rib 497 has been positioned in groove G2 whereby a portion of the lateral portions 428*a*, 428*b* is constrained which causes the original length and width L8, W7, respectively, to reduce to a new length and width L9, W8, respectively, resulting in a reduced opening 435 having a reduced perimeter 439. And by pressing the attachable loop portion 420 into the recess 423 even deeper until the annular rib 497 seats in either annular groove 3 or 4, even more of the lateral portions 428*a*, 428*b* are constrained resulting in an even smaller loop opening (not shown). An alternative retaining/adjustment means is shown in FIG. 32 whereby the rib 497*a* on the distal portion 432*a* is in the form of a male screw thread and the grooves G in the recess 423*a* are in the form of a female screw thread. In this case the user simply screws the attachable loop portion 420*a* in or out of the recess 423*a* at the proximal end 437*a* of the phallic portion 422*a*, which effects either a reduction or an increase, respectively, in the size of the loop opening 434*a*.

Figures 33, 34, 35:
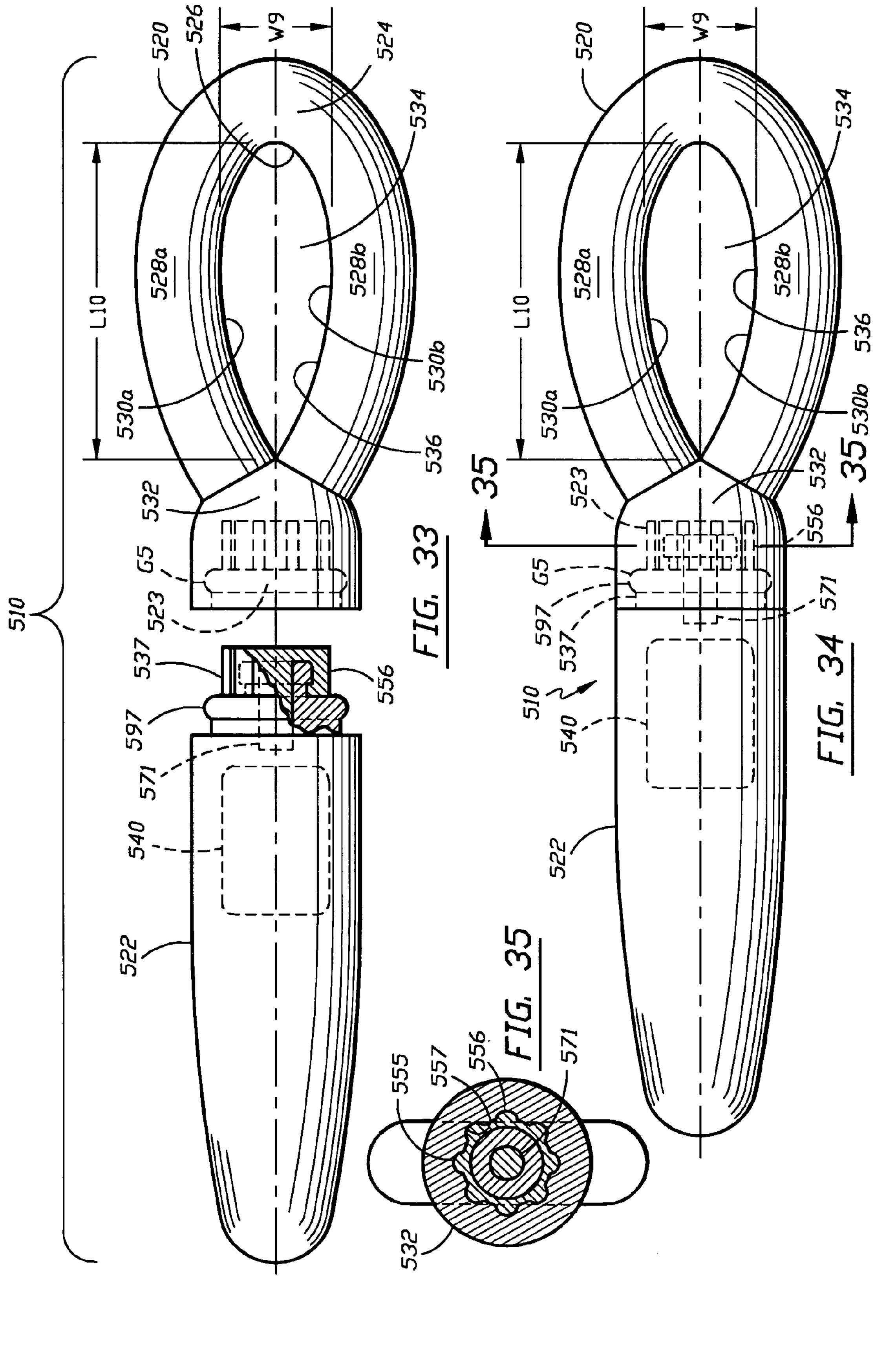
FIG. 33 shows a plan view of even yet another embodiment comprising a detachable phallic portion having an electric switch actuator at a proximal end, and an attachable loop portion, and a means for attachment.
FIG. 34 shows a plan view of the loop portion and the phallic portion of FIG. 33 assembled to one another.
FIG. 35 is a sectional view taken along lines 35-35 of FIG. 34 showing anti-slip means for rotating the electrical switch actuator.

There is shown in FIG. 33 a device 510 comprising a phallic portion 522 and an attachable loop portion 520 made of cylindrical elastomeric material, which may be tubular. The phallic portion 522 has a vibrator 540 therein that is connected to an internally disposed controller (not shown). The loop portion 520 comprises a proximal portion 524 and two lateral portions 528*a*, 528*b* that converge at a distal portion 532. Said proximal and lateral portions 524, 528*a*, 528*b*, respectively, have inner surfaces 526, 530*a*, 530*b*, respectively, that define an opening 534 having a length L10, a width W9, and a perimeter 536 at least 6.0 inches long. The length L10 is at least 1.5 times the width W9. The phallic portion 522 has a proximal end 537 that is configured to snugly engage a recess 523 in the distal portion 532 of the loop portion 520. The proximal end 537 has an annular rib 597 that is configured to seat in an annular groove G5 in the recess 523 when the proximal end 537 is fully seated in the recess 523. The annular rib 597 and annular groove G5 serve to function as a retaining means when the phallic portion 522 is assembled to the loop portion 520 as shown in FIG. 34. The proximal end 537 additionally includes a switch actuator 556 that is rotatable relative to the remainder of the phallic portion 522. The switch actuator 556 has a distally protruding central shaft 571 that actuates an electric switch (not shown) that turns the vibrator 540 on and off. The switch actuator 556 has a polar array of equally spaced longitudinal ribs 555 around its perimeter and the recess 523 includes a mating array of longitudinal grooves 557 that engage the longitudinal ribs 555 when the proximal end 537 is fully inserted in the recess 523 as shown in FIGS. 34 and 35. The longitudinal ribs 555 and longitudinal grooves 557 provide an anti-slipping means between the loop portion 520 and the switch actuator 556. This enables the user to turn the vibrator 540 on and off by rotating the loop portion 520 axially with respect to the phallic portion 522. Although the foregoing embodiment is described in conjunction with an internally disposed controller, a device may just as easily be configured with a remotely disposed controller, in which case an actuator would be omitted. Also, the retaining means could be reversed where a distal portion of a loop portion could have an external rib thereon and a proximal end of a phallic portion could contain a recess having a groove therein.

Figure 37:
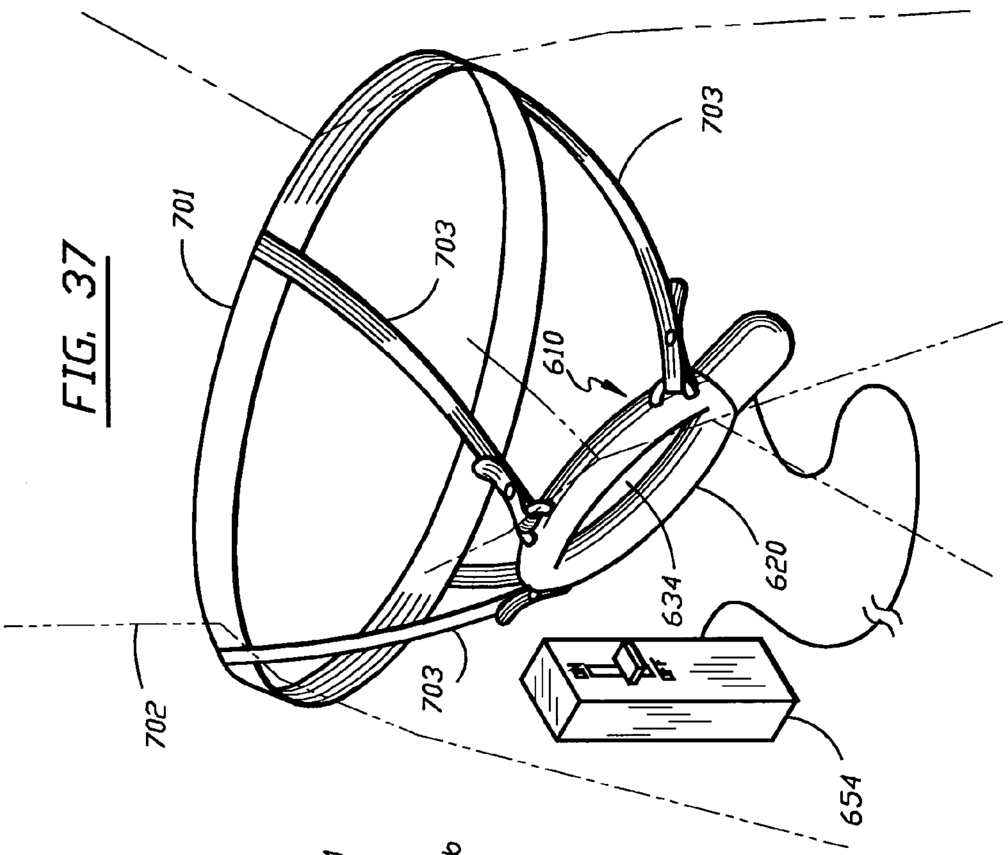
FIG. 37 shows the device of FIG. 32 with a harness attached positioning the device appropriately on a woman for use during intercourse.
Figure 36:
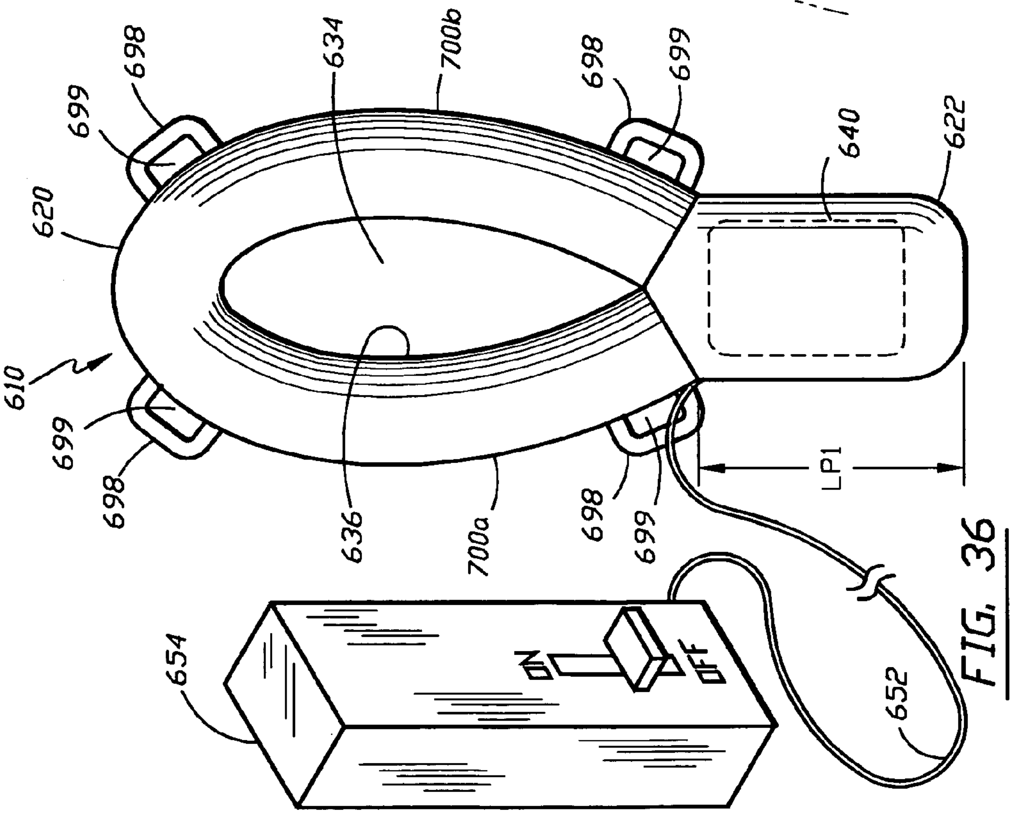
FIG. 36 shows even yet another embodiment of the device wherein the phallic portion is foreshortened and the device includes means for attaching a harness.

FIG. 36 shows even another embodiment of the present invention that comprises a device 610 configured for the express purpose of mutual stimulation to both a man and a woman during sexual intercourse. The device 610 includes a loop portion 620 made of cylindrical elastomeric material, which may be tubular, and an attached phallic portion 622 that contains a vibrator 640 therein. The vibrator 640 is interconnected with a controller 654 via a pair of electric wires 652. The phallic portion 622 has a length LP1 that is minimally adequate to enclose the vibrator 640. The loop portion 620 has an opening 634 that has a perimeter 636 that is at least 6.0 inches long. The device 610 also has loops 698 having openings 699 positioned on lateral surfaces 700*a*, 700*b* that provide means for the attachment of a harness 701, which is worn by a woman 702 represented in phantom line in FIG. 37. The harness 701 comprises elastic straps 703 configured to encircle the woman's legs and/or waist to efficiently bold the opening 634 of the loop portion 620 in place in front of the woman's 702 vagina.

Although the present invention has been herein described and illustrated in terms of particular embodiments, it is not limited to these embodiments. Other embodiments, equivalents, and modifications, which would still be encompassed by the invention, can be made by those skilled in the art, particularly in light of the foregoing teachings. Alternative embodiments, equivalents or modifications, may be included within the spirit and scope of the invention as defined by the claims.

The invention claimed is:

1. A sexual enhancement device comprising:

a distally disposed phallic portion containing a vibrator therein;

an attached proximally disposed loop portion made of an elastomeric material, said loop portion comprising a proximal portion, a distal portion and two lateral portions disposed therebetween, whereby said proximal portion, said lateral portions and said distal portion have a common innermost surface that defines an opening having an original width, an original length substantially greater than said width, and a perimeter at least five inches long, whereby upon introduction of a cylindrical object having a diameter greater than said width and a circumference less than said perimeter into said opening, said width increases, said length decreases, while said perimeter remains substantially the same and a free space remains between said innermost surface and the surface of said cylindrical object, whereupon removal of said cylindrical object said opening reassumes said original width and said original length, and a controller that functions to turn said vibrator on and off.

2. The device of claim 1, wherein said controller is disposed remotely from said device.

3. The device of claim 2, wherein said controller is connected to said vibrator by electric wires.

4. The device of claim 1, wherein a means is provided for the attachment of a harness.

5. The device of claim 4, wherein said means comprises an opening.

6. The device of claim 1, wherein said phallic portion is substantially round in cross-section, has a spherical radius at its distal end and is at least 3 inches long.

7. The device of claim 1, wherein said vibrator is disposed in a proximal end of said phallic portion adjacent said loop portion.

8. The device of claim 6, wherein said controller is located within said phallic portion and at least a portion of said phallic portion is detachable from a remaining portion thereby providing access to a battery compartment.

9. The device of claim 1, wherein said perimeter is at least 6.0 inches long.

10. The device of claim 1, wherein said elastomeric material is substantially round in cross-section with a diameter of at least 0.5 inch along a majority of its length.

11. The device of claim 1, wherein said width is less than 1.2 inches.

12. The device of claim 10, wherein said elastomeric material is tubular.

13. The device of claim 12, wherein said tubular material has a kink in said proximal portion.

14. The device of claim 9, additionally comprising a constraining means that encircles and constrains a portion of said loop portion thereby effecting a reduction in said opening.

15. The device of claim 6, said device being bilaterally symmetrical to both a first plane of symmetry and a perpendicularly disposed second plane of symmetry.

16. The device of claim 15, wherein at least a portion of said second plane of symmetry is curved.

17. The device of claim 8, said device additionally including an electric switch.

18. The device of claim 17, wherein said switch is actuated by rotating at least a portion of said detachable portion relative to said remaining portion.

19. A sexual enhancement device comprising:

a phallic portion containing a vibrator therein, said phallic portion having a proximal end with a recess therein;

a separable loop portion comprising a proximal portion and two lateral portions that converge at a distal portion, said portions having a common innermost surface that defines an opening having a length and a perimeter, said distal portion being configured to snugly fit at varying depths into said recess whereupon a portion of said loop portion is constrained by said recess thereby effecting a reduction in said length and, consequently, said perimeter of said opening.

20. The device of claim 19, said phallic portion and said loop portion including cooperative retaining means.

21. The device of claim 20, wherein said cooperative retaining means comprises a groove and a rib whereby said rib is configured to snuggly seat in said groove.

22. The device of claim 21, including additional grooves and/or ribs thereby providing a means to selectively adjust said length and perimeter of said opening.

23. The device of claim 19, wherein said recess includes a female screw thread and said distal portion includes a mating male screw thread.

24. The device of claim 23, whereby variably engaging said screw threads causes varying portions of said lateral portions to enter and be constrained by said recess thereby enabling a variable adjustment in the size of said opening.

25. The device of claim 19, said perimeter having a length of at least 6.0 inches.

26. A sexual enhancement device comprising:

a distally disposed phallic portion containing a vibrator therein, said phallic portion being at least 3.0 inches long and round in cross section along its length and having a spherical radius at a distal end; and an attached proximally disposed loop portion made of an elastomeric material and having an opening with a perimeter at least 6.0 inches long.

27. The device of claim 26, wherein said opening has a width less than 1.2 inches.

28. The device of claim 26, wherein a remotely disposed controller is connected to said vibrator by electric wires.

29. The device of claim 26, wherein said phallic portion contains a battery compartment.

30. The device of claim 26, wherein said elastomeric material is round in cross-section and has a diameter of at least 0.5 inch.

31. The device of claim 30, wherein said elastomeric material is tubular.

32. A sexual enhancement device comprising:

a loop portion made of an elastomeric material, said loop portion comprising a proximal portion, a distal portion and two lateral portions disposed therebetween, whereby said proximal portion, said lateral portions and said distal portion have a common innermost surface that defines an opening having a width, a length greater than said width, and a perimeter at least 5.0 inches long, whereby upon introduction of a cylindrical object having a diameter greater than said width and a circumference less than said perimeter into said opening, said width increases, said length decreases, while said perimeter remains substantially the same and a free space remains between said innermost surface and the surface of said cylindrical object, and said distal portion including retaining means for retaining an attachment comprising a vibrator.

33. The device of claim 32, wherein said length is at least 1.5 times greater than said width.

34. The device of claim 33, wherein said perimeter is at least 6.0 inches long.

35. The device of claim 32, wherein said retaining means comprises a groove.

36. The device of claim 32, wherein said retaining means comprises a rib.

37. The device of claim 32, wherein a major part of said lateral portions has a cross-section dimension of at least 0.5 inch.

38. The device of claim 37, wherein said lateral portions are tubular.

39. The device of claim 32, said device additionally including a phallic portion containing a vibrator therein, said phallic portion attached to said loop portion by said retaining means and comprising a switch that functions to turn said vibrator on and off.

40. The device of claim 39 wherein said loop portion and said phallic portion comprise cooperative anti-slipping means that enable actuation of said switch upon rotating said loop portion relative to said phallic portion.

41. A sexual enhancement device comprising:

a loop portion made of an elastomeric material and comprising a proximal portion, a distal portion and two lateral portions disposed therebetween, whereby said proximal, distal, and lateral portions have a common innermost surface that defines an opening having an original shape comprising a width, a length greater than said width, and a perimeter, whereupon introduction of a cylindrical object having a circumference of five inches into said opening said lateral portions bilaterally contact said cylindrical object and said opening acquires a new shape whereby said width increases, said length decreases, while said perimeter remains substantially the same and a free space remains between said innermost surface and the surface of said cylindrical object such that said cylindrical object is not substantially circumferentially constricted by said loop portion and said cylindrical object remains equally slidable in either direction within said opening, and whereupon removal of said cylindrical object said opening returns to said original shape, and an adjoined means for imparting vibrations to said loop portion.

42. The device of claim 41 wherein a majority of said loop portion comprises a cross- sectional dimension of at least 0.5 inches.

43. The device of claim 41, wherein said lateral portions are tubular.

44. The device of claim 41 wherein said perimeter is at least 6 inches long.

45. The device of claim 44 additionally comprising an adjustable constraining means that encircles and constrains said lateral portions adjacent said distal portion whereby a reduction in said width, length and perimeter is effected by adjusting said constraining means toward said proximal portion and, conversely, an increase in said width, length and perimeter is effected by adjusting said constraining means away from said proximal portion.

* * * * *